(12) United States Patent
Russo et al.

(10) Patent No.: US 10,342,650 B2
(45) Date of Patent: Jul. 9, 2019

(54) SKIRTED HERNIA REPAIR DEVICE

(71) Applicant: Covidien LP, Mansfield, MA (US)

(72) Inventors: Mark Russo, Plantsville, CT (US); Raylene Worthington, Wakefield, RI (US)

(73) Assignee: Covidien LP, Mansfield, MA (US)

( * ) Notice: Subject to any disclaimer, the term of this patent is extended or adjusted under 35 U.S.C. 154(b) by 758 days.

(21) Appl. No.: 14/453,640

(22) Filed: Aug. 7, 2014

(65) Prior Publication Data

US 2015/0094743 A1    Apr. 2, 2015

Related U.S. Application Data

(60) Provisional application No. 61/883,450, filed on Sep. 27, 2013.

(51) Int. Cl.
*A61F 2/00* (2006.01)

(52) U.S. Cl.
CPC .... *A61F 2/0063* (2013.01); *A61F 2002/0072* (2013.01); *A61F 2220/0075* (2013.01)

(58) Field of Classification Search
CPC .... A61F 2/0063; A61F 2/0077; A61F 2/0805; A61F 2/0811; A61F 2002/0068; A61F 2002/0072; A61F 2002/0829; A61F 2002/0864; A61F 2002/0888; A61F 2002/30062; A61F 2002/30093; A61F 2002/30153; A61F 2002/30156; A61F 2002/30181; A61F 2210/0004; A61F 2210/0076; A61F 2210/0019; A61F 2250/0051; A61F 2230/0019; A61F 2230/0023; A61F 2230/006; A61B 17/06133; A61B 17/06166; A61B 17/0487; A61B 17/0469; A61B 2017/06142; A61B 2017/06176; A61B 2017/06028; A61B 2017/0619; B29C 66/81463

See application file for complete search history.

(56) References Cited

U.S. PATENT DOCUMENTS

| | | | |
|---|---|---|---|
| 4,932,961 | A | 6/1990 | Wong et al. |
| 4,961,498 | A | 10/1990 | Kalinski et al. |
| 4,967,902 | A | 11/1990 | Sobel et al. |
| 5,002,564 | A | 3/1991 | McGregor et al. |
| 5,002,565 | A | 3/1991 | McGregor |
| 5,030,228 | A | 7/1991 | Wong et al. |

(Continued)

FOREIGN PATENT DOCUMENTS

FR    2929834 A1    10/2009

OTHER PUBLICATIONS

Definition of "Fixed" as defined by Dictionary.com, accessed on Mar. 4, 2018.*

(Continued)

*Primary Examiner* — David C Eastwood
*Assistant Examiner* — Mohamed G Gabr

(57) ABSTRACT

The present disclosure relates to skirted hernia repair devices which includes at least a first mesh layer having a first side, a second side, and an outer peripheral edge, a skirt mesh layer positioned on the first side of the first mesh layer, the skirt mesh layer having an inner peripheral edge defining an opening in the skirt mesh layer, and, at least one reinforcement member that prevents the skirt mesh layer from inverting.

9 Claims, 11 Drawing Sheets

(56) References Cited

U.S. PATENT DOCUMENTS

| | | |
|---|---|---|
| 5,052,551 A | 10/1991 | Cerwin et al. |
| 5,056,658 A | 10/1991 | Sobel et al. |
| 5,099,994 A | 3/1992 | Kalinski et al. |
| 5,100,432 A | 3/1992 | Matsutani |
| 5,131,533 A | 7/1992 | Alpern |
| 5,165,217 A | 11/1992 | Sobel et al. |
| 5,178,628 A | 1/1993 | Otsuka et al. |
| 5,179,818 A | 1/1993 | Kalinski et al. |
| 5,180,053 A | 1/1993 | Cascio et al. |
| 5,192,483 A | 3/1993 | Kilgrow et al. |
| 5,213,210 A | 5/1993 | Cascio et al. |
| 5,222,976 A | 6/1993 | Yoon |
| 5,230,424 A | 7/1993 | Alpern et al. |
| 5,236,083 A | 8/1993 | Sobel et al. |
| 5,258,000 A | 11/1993 | Gianturco |
| 5,263,585 A | 11/1993 | Lawhon et al. |
| 5,263,974 A | 11/1993 | Matsutani et al. |
| 5,271,495 A | 12/1993 | Alpern |
| 5,284,240 A | 2/1994 | Alpern et al. |
| 5,330,441 A | 7/1994 | Prasad et al. |
| 5,330,503 A | 7/1994 | Yoon |
| 5,342,376 A | 8/1994 | Ruff |
| 5,342,397 A | 8/1994 | Guido |
| 5,350,060 A | 9/1994 | Alpern et al. |
| 5,403,344 A | 4/1995 | Allen |
| 5,407,071 A | 4/1995 | Lawhon et al. |
| 5,425,747 A | 6/1995 | Brotz |
| 5,472,081 A | 12/1995 | Kilgrow et al. |
| 5,575,382 A | 11/1996 | Sobel et al. |
| 5,584,859 A | 12/1996 | Brotz |
| 5,593,441 A | 1/1997 | Lichtenstein et al. |
| 5,628,395 A | 5/1997 | Daniele et al. |
| 5,634,931 A | 6/1997 | Kugel |
| 5,645,568 A | 7/1997 | Chervitz et al. |
| 5,655,652 A | 8/1997 | Sobel et al. |
| 5,675,961 A | 10/1997 | Cerwin et al. |
| 5,683,416 A | 11/1997 | McGregor et al. |
| 5,704,469 A | 1/1998 | Daniele et al. |
| 5,730,732 A | 3/1998 | Sardelis et al. |
| 5,743,917 A | 4/1998 | Saxon |
| 5,749,897 A | 5/1998 | Matsutani et al. |
| 5,769,864 A | 6/1998 | Kugel |
| 5,788,062 A | 8/1998 | Cerwin et al. |
| 5,797,961 A | 8/1998 | Smith et al. |
| 5,887,706 A | 3/1999 | Pohle et al. |
| 5,893,880 A | 4/1999 | Egan et al. |
| 5,906,273 A | 5/1999 | Pohle et al. |
| 5,913,875 A | 6/1999 | Smith et al. |
| 5,916,225 A | 6/1999 | Kugel |
| 5,918,733 A | 7/1999 | Cerwin et al. |
| 5,931,855 A | 8/1999 | Buncke |
| 5,964,765 A | 10/1999 | Fenton, Jr. et al. |
| 6,047,815 A | 4/2000 | Cerwin et al. |
| 6,076,659 A | 6/2000 | Baumgartner et al. |
| 6,098,796 A | 8/2000 | Januzeli et al. |
| 6,105,339 A | 8/2000 | Pohle et al. |
| 6,106,545 A | 8/2000 | Egan |
| 6,120,539 A | 9/2000 | Eldridge et al. |
| 6,135,272 A | 10/2000 | Sobel et al. |
| 6,135,385 A | 10/2000 | Martinez de Lahidalga |
| 6,171,318 B1 | 1/2001 | Kugel et al. |
| 6,174,320 B1 | 1/2001 | Kugel et al. |
| 6,174,324 B1 | 1/2001 | Egan et al. |
| 6,176,863 B1 | 1/2001 | Kugel et al. |
| 6,217,591 B1 | 4/2001 | Egan et al. |
| 6,224,616 B1 | 5/2001 | Kugel |
| 6,241,747 B1 | 6/2001 | Ruff |
| 6,264,675 B1 | 7/2001 | Brotz |
| 6,270,517 B1 | 8/2001 | Brotz |
| 6,270,530 B1 | 8/2001 | Eldridge et al. |
| 6,280,453 B1 | 8/2001 | Kugel et al. |
| 6,290,708 B1 | 9/2001 | Kugel et al. |
| 6,358,271 B1 | 3/2002 | Egan et al. |
| 6,394,269 B1 | 5/2002 | Rudnick et al. |
| 6,409,743 B1 | 6/2002 | Fenton, Jr. |
| 6,464,071 B2 | 10/2002 | Baumgartner |
| 6,478,809 B1 | 11/2002 | Brotz |
| 6,481,568 B1 | 11/2002 | Cerwin et al. |
| 6,481,569 B1 | 11/2002 | Alpern |
| 6,497,650 B1 | 12/2002 | Nicolo |
| 6,533,112 B2 | 3/2003 | Warnecke |
| 6,599,310 B2 | 7/2003 | Leung et al. |
| 6,644,469 B2 | 11/2003 | Alpern |
| 6,652,595 B1 | 11/2003 | Nicolo |
| 6,669,705 B2 | 12/2003 | Westhaver et al. |
| 6,736,823 B2 | 5/2004 | Darois et al. |
| 6,773,450 B2 | 8/2004 | Leung et al. |
| 7,056,331 B2 | 6/2006 | Kaplan et al. |
| 7,090,111 B2 | 8/2006 | Egan et al. |
| 7,156,804 B2 | 1/2007 | Nicolo |
| 7,226,468 B2 | 6/2007 | Ruff |
| 7,371,253 B2 | 5/2008 | Leung et al. |
| 7,806,905 B2 | 10/2010 | Ford et al. |
| 7,824,420 B2 | 11/2010 | Eldridge et al. |
| 2003/0078602 A1* | 4/2003 | Rousseau .............. A61F 2/0063 606/151 |
| 2003/0130745 A1* | 7/2003 | Cherok ................ A61F 2/0063 623/23.72 |
| 2007/0088391 A1* | 4/2007 | McAlexander ..... A61L 27/3633 606/232 |
| 2007/0299538 A1* | 12/2007 | Roeber ................ A61F 2/0063 623/23.72 |
| 2009/0270999 A1* | 10/2009 | Brown ................ A61F 2/0063 623/23.72 |
| 2013/0103058 A1 | 4/2013 | Gobran |
| 2014/0025093 A1* | 1/2014 | Horton ................ A61F 2/0063 606/151 |

OTHER PUBLICATIONS

European Search Report, Application No. 14 18 5216 dated Jan. 28, 2015.

Australian Examination Report for Application No. 2014213511 dated May 21, 2018, 3 pages.

Australian Examination Report issued in Application No. 2014213511 dated Aug. 17, 2018.

Examination Report No. 3 issued in corresponding Australian application No. 2014213511 dated Dec. 18, 2019, 3 pages.

* cited by examiner

SKIRTED HERNIA REPAIR DEVICE

CROSS-REFERENCE TO RELATED APPLICATIONS

This application claims the benefit of and priority to U.S. Provisional Patent Application No. 61/883,450, filed Sep. 27, 2013, the entire disclosure of which is incorporated by reference herein.

BACKGROUND

Technical Field

The present disclosure relates to hernia repair devices and, more particularly, to reinforced skirted mesh for use in hernia repair.

Background of Related Art

Hernias may be caused by defects in the muscle layer of the abdomen. Historically, attempts to reconstruct the abdominal wall muscles have been associated with a high recurrence rate.

Implantable devices for repairing hernia have been known for many years. They may be used to repair damaged tissue and to provide structure for supporting surrounding tissue.

The most basic form of device that can be used for hernia repair is a piece of mesh or any other flexible flat material that is strong enough to be affixed to the surrounding damaged tissue.

The key objective of a hernia repair procedure is to patch the hernia defect and to reinforce the surrounding weak muscle layer.

A number of mesh designs and techniques have been introduced to allow surgeons to improve the outcome of hernia repair procedures and to avoid some of the common complications.

Skirted hernia repair devices have become somewhat popular because they offer added strength and a lower recurrence rate, as compared to the older non-skirted repair devices.

However, the major challenge presented by the skirted hernia repair devices is the difficulty of maintaining the skirted repair device flat in the field, until it is properly secured to the surrounding tissue. More specifically, skirted hernia repair devices may be easily inverted, i.e., turned inside-out, prior to and/or during implantation, and more specifically, while a surgeon attempts to secure the skirted device to the tissue.

It would be beneficial to provide reinforced skirted hernia repair devices that are less likely to be inverted prior to and/or during implantation and more specifically, while a surgeon attempts to secure the skirted device to the tissue.

SUMMARY

In accordance with one embodiment of the present disclosure, a skirted hernia repair device having multiple skirted sections is provided. The skirted hernia repair device includes a first mesh layer, a skirt mesh layer and at least one reinforcement member. The first mesh layer includes at least a first side, a second side, and an outer peripheral edge. The skirt mesh layer is positioned on the first side of the first mesh layer, and the skirt mesh layer includes an outer peripheral edge and an inner peripheral edge. The inner peripheral edge of the skirt mesh layer defines an opening in the skirt mesh layer. At least one reinforcement member connects the first mesh layer to the skirt mesh layer. The reinforcement member is positioned near the inner peripheral edge to prevent the skirt mesh layer from inverting.

In another embodiment, a skirted hernia repair device is described which includes a first planar mesh layer, a skirted section, and a plurality of reinforcement members. The first planar mesh layer has a first side, a second side and an outer peripheral edge. The skirted section is located on the first side of the first planar mesh layer near the outer peripheral edge. The plurality of reinforcement members connect a portion of the pocket to the first planar mesh layer to prevent the pocket from inverting.

Methods of using the skirted hernia repair devices are also described. In one embodiment, a method for repairing a tissue defect is described which includes: providing a skirted hernia repair device, positioning the skirted hernia repair device within a tissue defect such that a first mesh layer extends across the defect; and, securing the skirted hernia repair device to tissue. The skirted hernia repair device includes a first mesh layer, a skirt mesh layer, and at least one reinforcement member that connects the first mesh layer to the skirt mesh layer to prevent the skirt mesh layer from inverting. The first mesh layer includes a first side, a second side, and an outer peripheral edge. The skirt mesh layer is positioned on the first side of the first mesh layer; the skirt mesh layer includes an inner peripheral edge defining an opening. At least one reinforcement member that connects the first mesh layer to the skirt mesh layer to prevent the skirt mesh layer from inverting.

BRIEF DESCRIPTION OF THE DRAWINGS

Various embodiments of the present disclosure are described herein with reference to the drawings wherein.

DETAILED DESCRIPTION

Figure 1A:
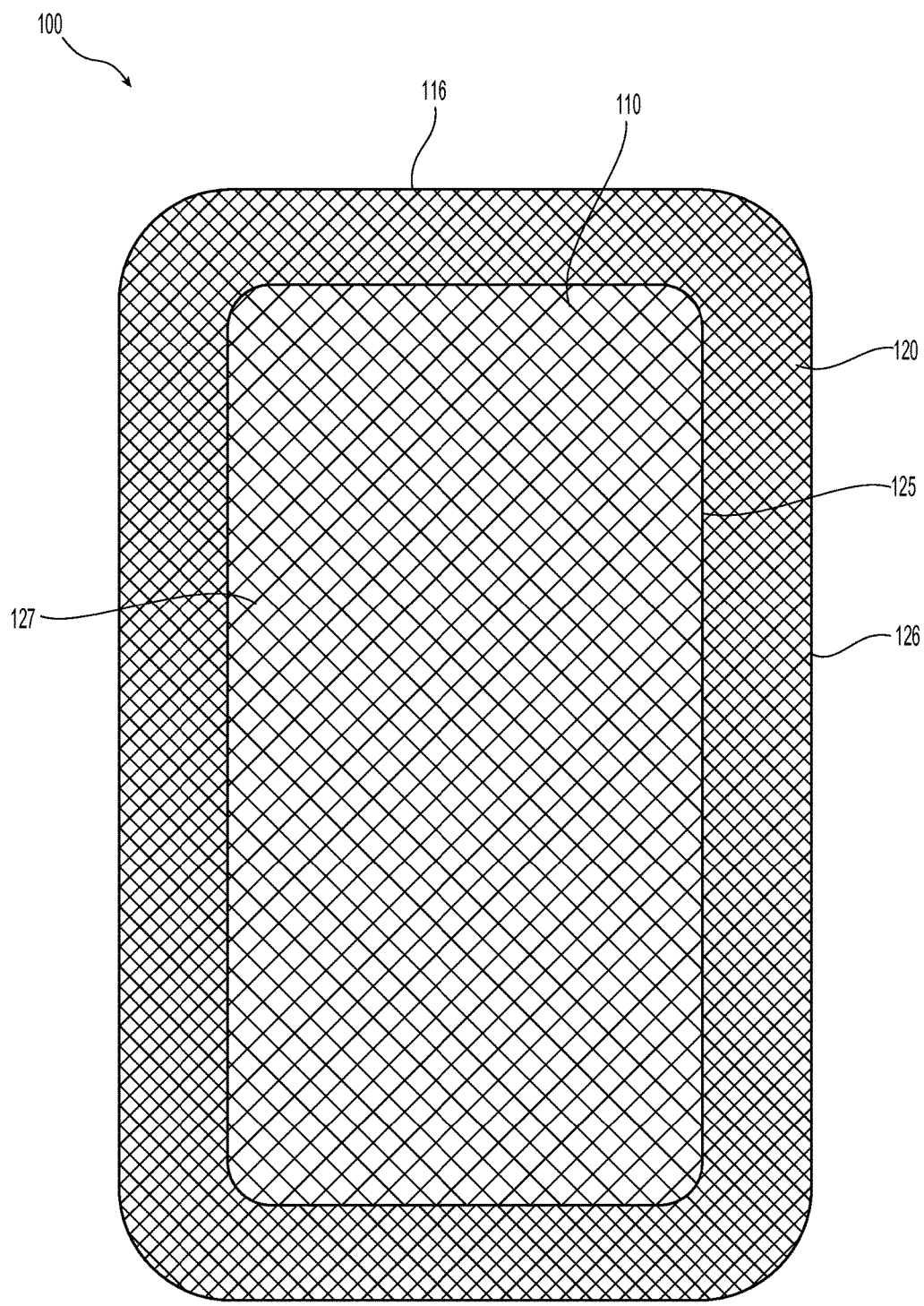
FIGS. 1A and 1C are each a top view of a prior art skirted hernia repair device.

The present disclosure describes skirted hernia repair devices. The term "hernia repair devices" is not intended to be limited to devices suitable strictly for hernia repair but rather is intended to include any procedure, i.e., open, laparoscopic, endoluminal, intravaginal, NOTES, etc., for the repair of hernias, prolapses, fistulas, stomas, and the like. In particular embodiments, the skirted repair devices described herein may be used in intraperitoneal onlay procedures, and more particularly, open intraperitoneal onlay procedures.

Turning now to the figures, embodiments of the present disclosure are described in detail with reference to the figures wherein like reference numerals identify similar or identical elements.

Figure 1B:
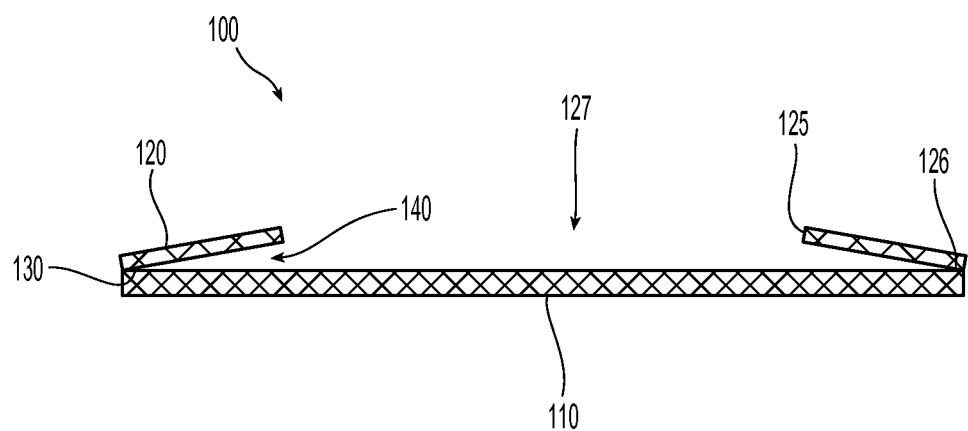
FIG. 1B is a side view of the prior art skirted hernia repair device depicted in FIG. 1A.
Figure 1C:
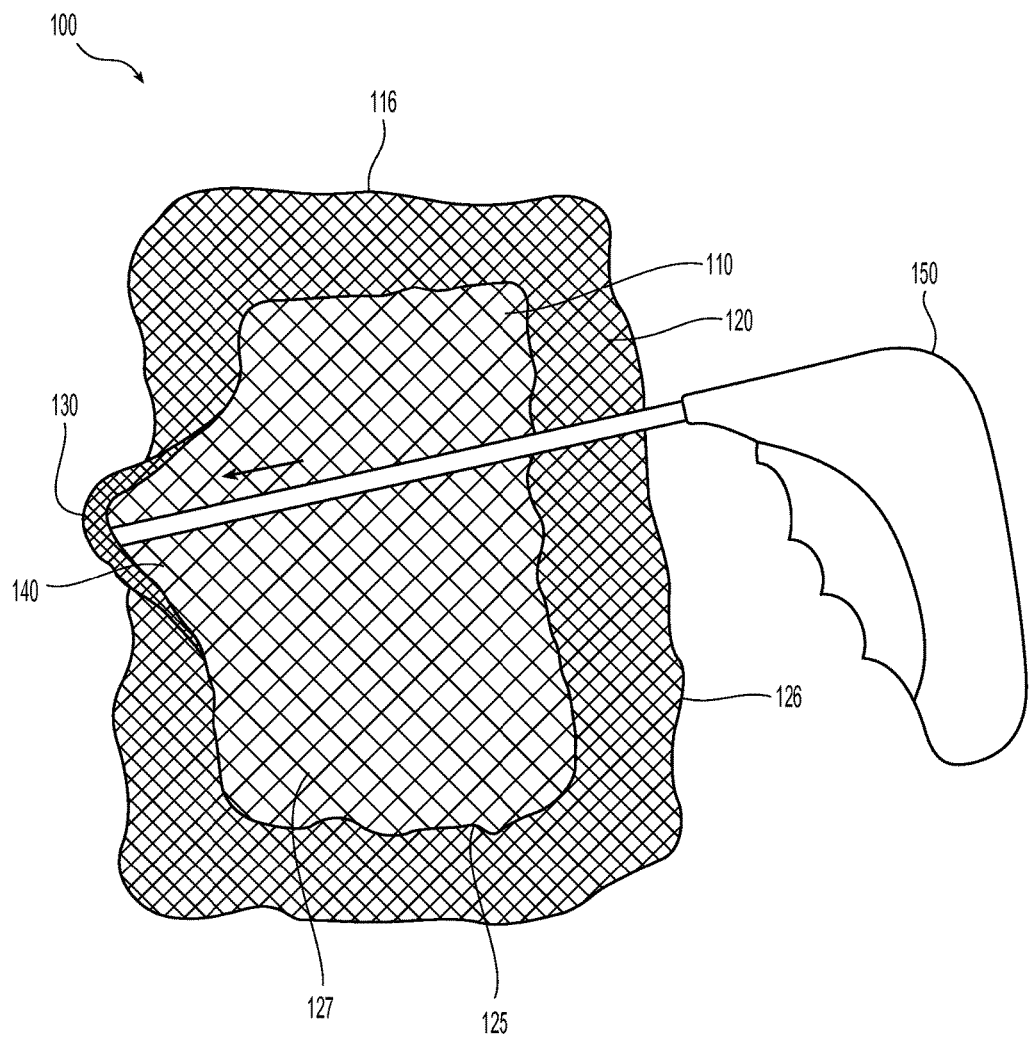

FIGS. 1A-1C show a prior art skirted hernia repair device 100. The device includes a first mesh layer 110 suitable for extending across a tissue opening and a skirt mesh layer 120 having an inner peripheral edge 125 which defines opening 127. Outer peripheral edge 116 of first mesh layer 110 is attached to outer peripheral edge 126 of skirt mesh layer 120 by seam 130. Pocket 140 is formed between first mesh layer 110 and skirt mesh layer 120, wherein pocket 140 extends from inner peripheral edge 125 of skirt mesh layer to seam 130 and/or outer peripheral edge 126 of skirt mesh layer 120. As one skilled in the art may appreciate, in FIG. 1B, skirt mesh layer 120 is shown in a configuration which is spaced apart from first mesh layer 110 to better illustrate pocket 140, but is not intended to suggest that skirt mesh layer 120 is permanently configured in this manner.

As illustrated in FIG. 1C, fastening device 150 may be used to secure skirted hernia repair device 100 to tissue. During implantation, in an open or laparoscopic procedure, a patient's tissue may prevent direct visualization of fastening device 150 and/or skirted hernia repair device 100. In such instances, a surgeon may simply slide fastening device 150 laterally across first mesh layer 110 (as indicated by the arrow) and into pocket 140 until fastening device 150 gets caught or snagged on seam 130 and/or outer peripheral edges 116, 126 of either layer of the device 100. At which time, the surgeon may fire fastening device 150 and deliver a fastener (not shown) in the vicinity of pocket 140 and through device 100, thereby securing device 100 to the tissue in the vicinity of pocket 140 and/or outer peripheral edge 116, 126 of either layer of device 100. However, in some instances as illustrated in FIG. 1C, skirt mesh layer 120 may be inverted or turned inside out when fastening device 150 is slid laterally across first mesh layer 110 and into pocket 140. If inverted, fastening device 150 may not catch or snag on seam 130 and/or outer peripheral edges 116, 126 of either layer of device 100. Thus the surgeon can not determine the proper position of fastening device 150 relative to the skirted hernia repair device 100. As a result of the inverted pocket or mesh, and without direct visualization, it may be difficult for the surgeon to know when to fire fastening device 150.

Figure 2A:
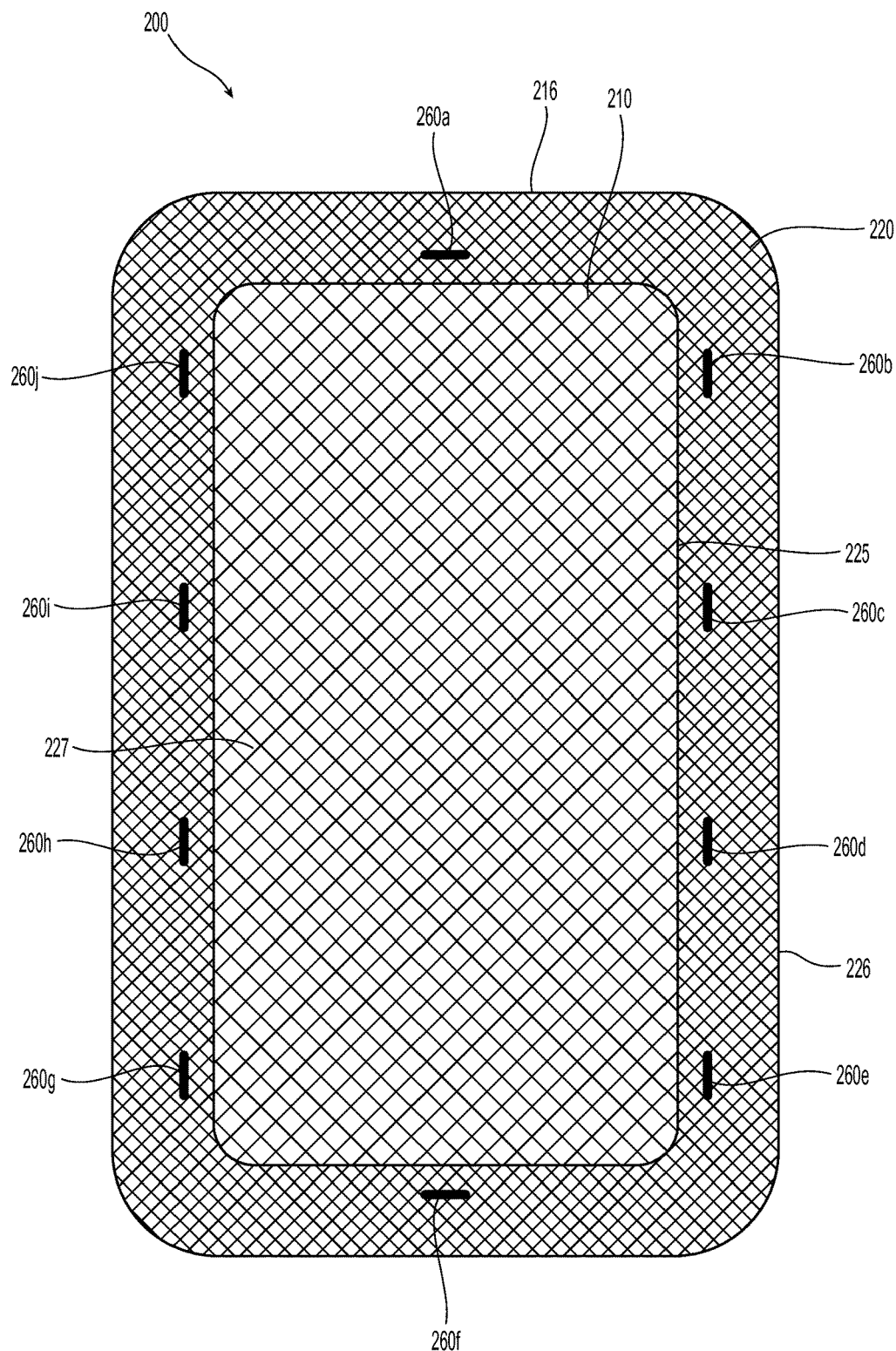
FIGS. 2A and 2B are each a top view of at least one embodiment of a skirted hernia repair device in accordance with the present disclosure.
Figure 2B:
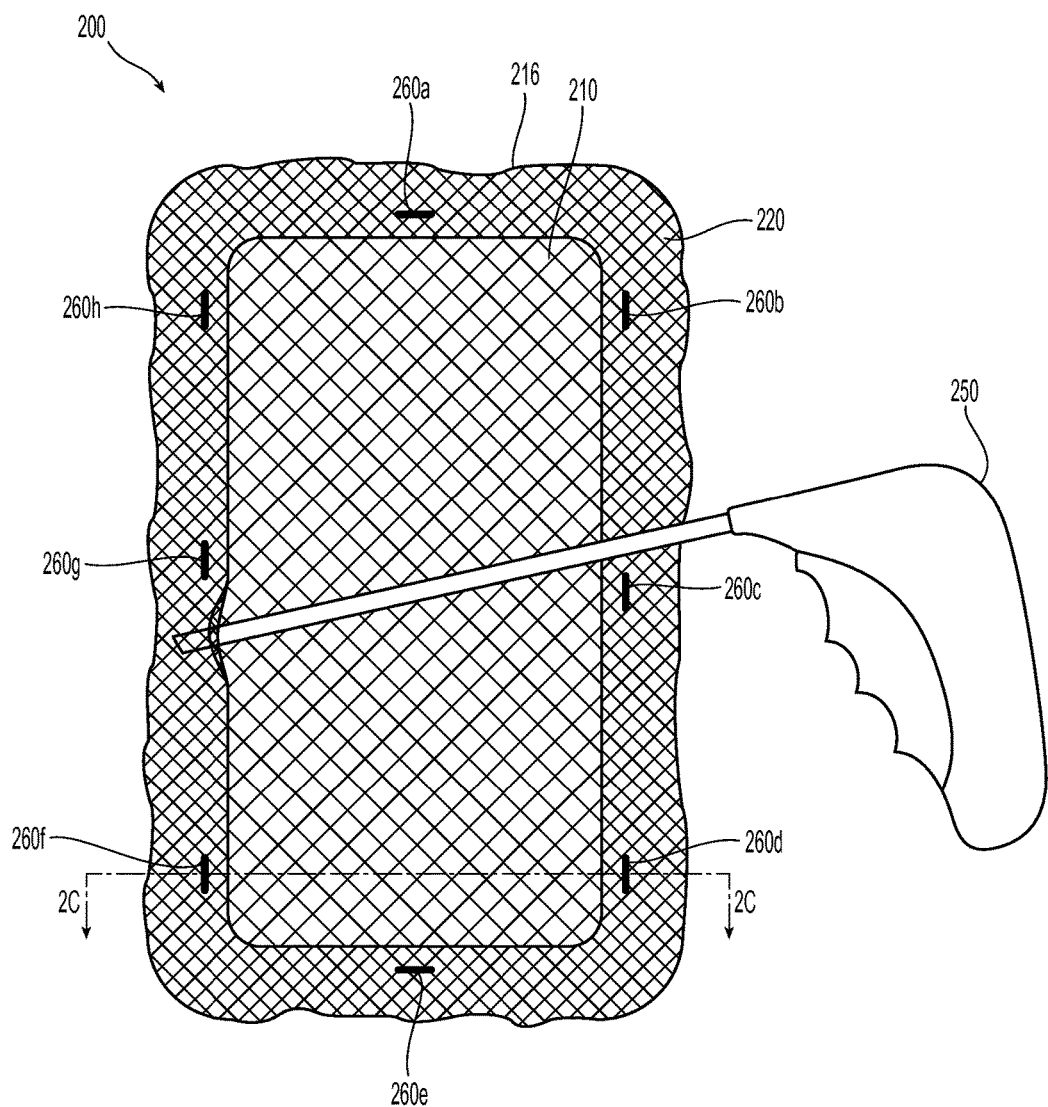
Figure 2C:
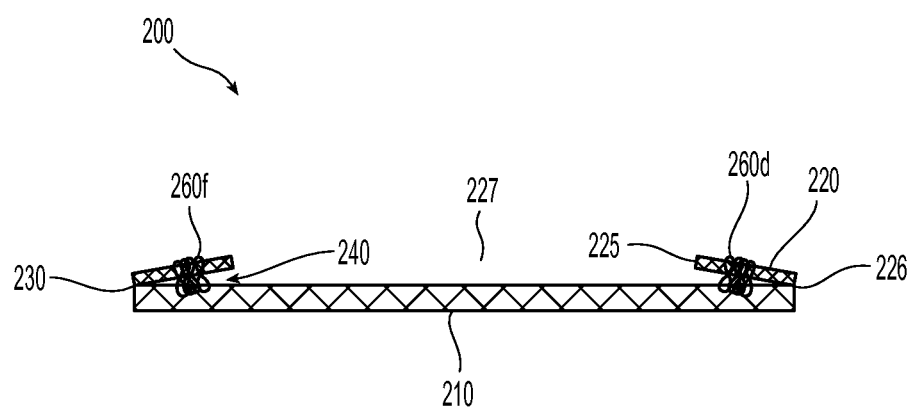
FIG. 2C is a side view of the embodiment depicted in FIGS. 2A and 2B.

FIGS. 2A-2C depict a skirted hernia repair device 200 of the present disclosure wherein pocket 240 and/or skirt mesh layer 220 is reinforced by at least one reinforcement member 260a-j which is preferably located in the vicinity of inner peripheral edge 225 to prevent skirt mesh layer 220 and/or pocket 240 from inverting. Skirted hernia repair device 200 includes a first mesh layer 210 suitable for extending across a tissue opening and a skirt mesh layer 220 having an inner peripheral edge 225 which defines opening 227. Outer peripheral edge 216 of first mesh layer 210 is attached to outer peripheral edge 226 of skirt mesh layer 220 by seam or fold 230. Pocket 240 is formed between first mesh layer 210 and skirt mesh layer 220, wherein pocket 240 extends from inner peripheral edge 225 of skirt mesh layer to seam or fold 230 and/or outer peripheral edge 226 of skirt mesh layer 220. The skirt mesh layer may extend along the entire periphery or only a portion of the peripheral edge 225 of the first mesh layer 210.

As further depicted in FIGS. 2A and 2C, skirted hernia repair device 200 may include a plurality of reinforcement members 260a-j which are positioned around inner peripheral edge 225 of skirt mesh layer 220 to form distinct skirt sections 280a-j.

As illustrated in FIG. 2B, fastening device 250 may be used to secure skirted hernia repair device 200 to tissue. During implantation, in an open or laparoscopic procedure, a patient's tissue may prevent direct visualization of fastening device 250 and/or skirted hernia repair device 200. In such instances, a surgeon may simply slide fastening device 250 laterally across first mesh layer 210 and into pocket 240 until the distal end of fastening device 250 gets caught or snagged on seam or fold 230 and/or outer peripheral edges 216, 226 of either layer of the device 200. At which time, the surgeon may fire fastening device 250 and deliver a fastener (not shown) in the vicinity of pocket 240 and through device 200, thereby securing device 200 to the tissue in the vicinity of skirt mesh layer 220 and/or outer peripheral edge 216, 226 of either layer of device 200. As further illustrated in FIG. 2B, reinforcement members 260a-j of skirted hernia repair device 200 secure skirt mesh layer 220 to first mesh layer 210 intermittently around inner peripheral edge 225 forming skirt sections 280a-j and preventing skirt mesh layer 220 and/or pocket 240 from being inverted prior to and/or during implantation. A more stable pocket 240 enhances a surgeon's ability to identify the proper placement of a fastener to secure device 200 and into the tissue. As a result, recurrence rates decrease due to more stable implants and surgical time decreases due to more efficient procedures.

As depicted in FIG. 2C, reinforcement members 260d, 260f attach or connect first mesh layer 210 to skirt mesh layer 220 in the vicinity of inner peripheral edge 225. In embodiments, as further depicted in FIG. 2C, reinforcement members 260d, 260f may be positioned on top of skirt mesh layer 220 and extend through pocket 240 to connect to first mesh layer 210. In embodiments, as further depicted in FIG. 2, reinforcement members 260 may be filaments which can be woven, braided, knitted, non-woven, and the like, to attach skirt mesh layer 220 to first mesh layer 210 in the vicinity of inner peripheral edge 225. In embodiments, the reinforcement members 260 may not extend laterally beyond inner peripheral edge 225 thereby maintaining a continuous and/or uninterrupted inner peripheral edge 225, as shown in FIGS. 2A-2C.

In addition to using reinforcement members, or as a substitute for the reinforcement members, the skirt sections may be formed by ultrasonic welding or using adhesives to bond the skirt mesh layer 220 to first mesh layer 210 at discreet locations such as those where a reinforcement member would be positioned.

Figure 3A:
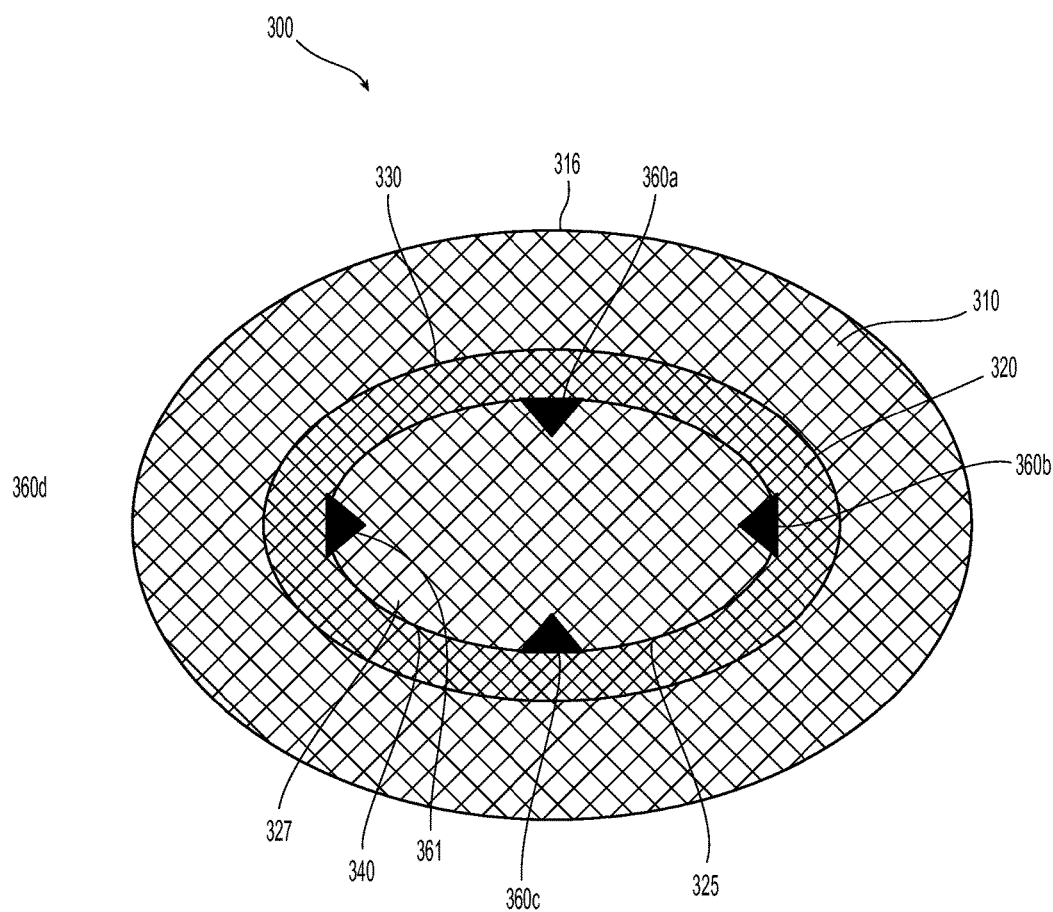
FIG. 3A is a top view of at least one embodiment of a skirted hernia repair device in accordance with the present disclosure.
Figure 3B:
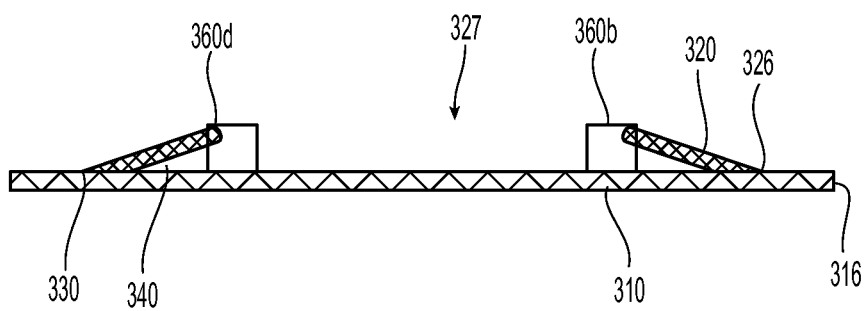
FIG. 3B is a side view of the embodiment depicted in FIG. 3A.

FIGS. 3A-3B illustrate a skirted hernia repair device 300 of the present disclosure wherein pocket 340 and/or skirt mesh layer 320 is by at least one reinforcement member 360a-d located in the vicinity of inner peripheral edge 325 to prevent skirt mesh layer 320 from inverting. Skirted hernia repair device 300 includes first mesh layer 310 suitable for extending across a tissue opening and skirt mesh layer 320 having an inner peripheral edge 325 which defines opening 327. In FIG. 3A, outer peripheral edge 326 of skirt mesh layer 320 is attached to first mesh layer 310, but not along outer peripheral edge 316 of first mesh layer 310 by seam or fold 330. Pocket 340 is formed between first mesh layer 310 and skirt mesh layer 320, wherein pocket 340 extends from inner peripheral edge 325 of skirt mesh layer to seam 330 and/or outer peripheral edge 326 of skirt mesh layer 320.

In embodiments, as further depicted in FIG. 3A, skirted hernia repair device 300 may include a plurality of reinforcement members 360a-d, non-symmetrically positioned around inner peripheral edge 325 of skirt mesh layer 320. In embodiments, as further depicted in FIG. 3A, reinforcement members 360a-d may extend inwardly from skirt mesh layer 320 over inner peripheral edge 325 and onto a surface of first mesh layer 310, thereby over-lapping both first mesh layer 310 and skirt mesh layer 320 intermittently along a portion of inner peripheral edge 325.

As depicted in FIG. 3B, reinforcement members 360b, 360d attach or connect first mesh layer 310 to skirt mesh layer 320 in the vicinity of inner peripheral edge 325. In embodiments, as further depicted in FIG. 3B, reinforcement members 360b, 360d may be positioned on top of skirt mesh layer 320 and extend through pocket 340 to connect to first mesh layer 310. In embodiments, as further depicted in FIG. 3B, reinforcement members 360 may be polymeric tabs that may be formed on device 300 using any suitable process including, but limited to, extrusion, molding, melt-processing, heat-pressing, ultrasonic, welding, sealing, fusing, and the like.

Still referring to FIGS. 3A and 3B, reinforcement members 360a-d may include a beveled or rounded surface 361 which can act as a guide to direct a fastening device (not shown) into pocket 340. It is envisioned that in embodiments wherein the reinforcement member can also act as a guide for the fastening device, the likelihood of the fastening device entering the pocket may be increased. Also, the likelihood of a surgeon mistaking the reinforcement member for the seam may be decreased.

Figure 4A:
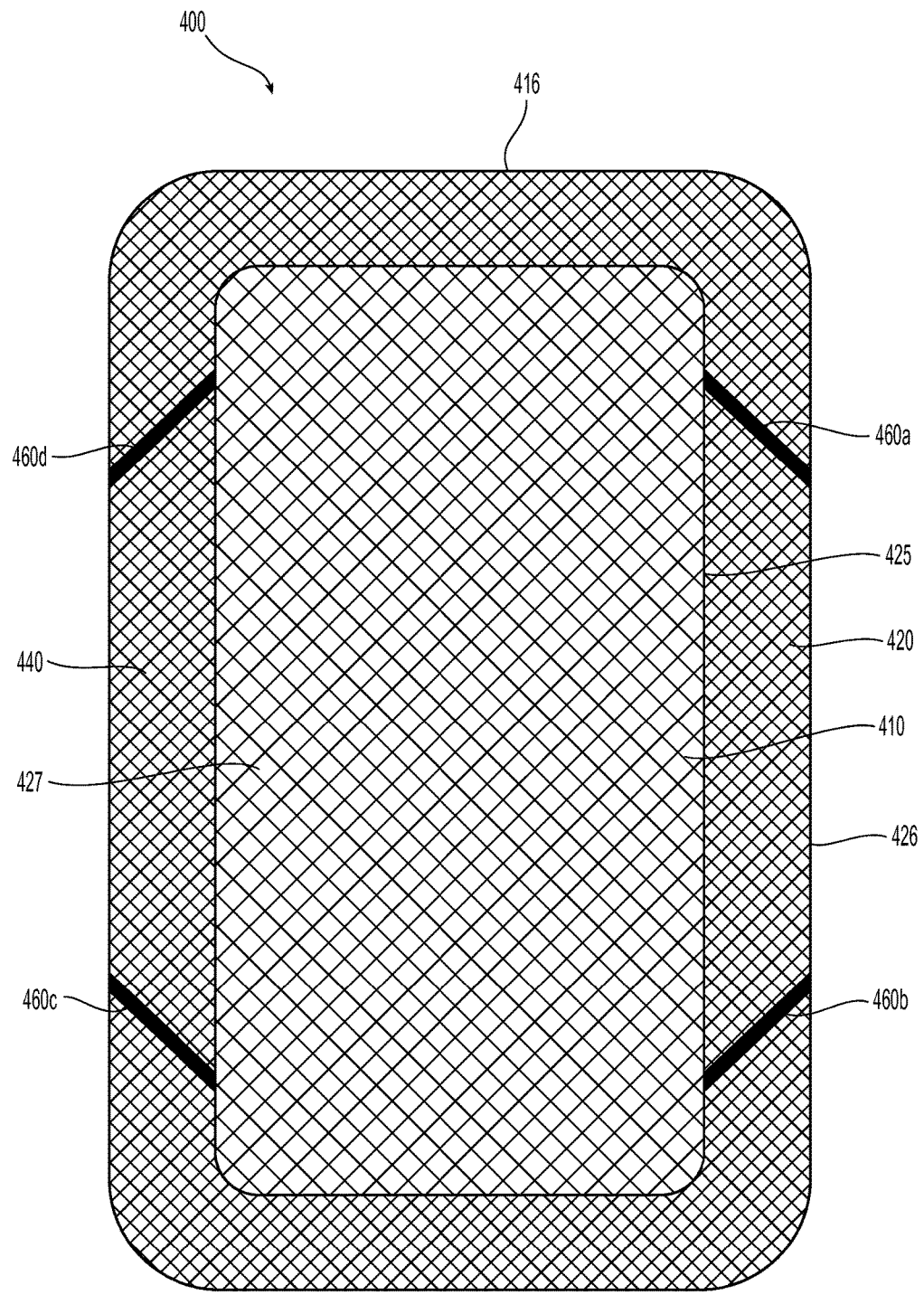
FIG. 4A is a top view of at least one embodiment of a skirted hernia repair device in accordance with the present disclosure.
Figure 4B:
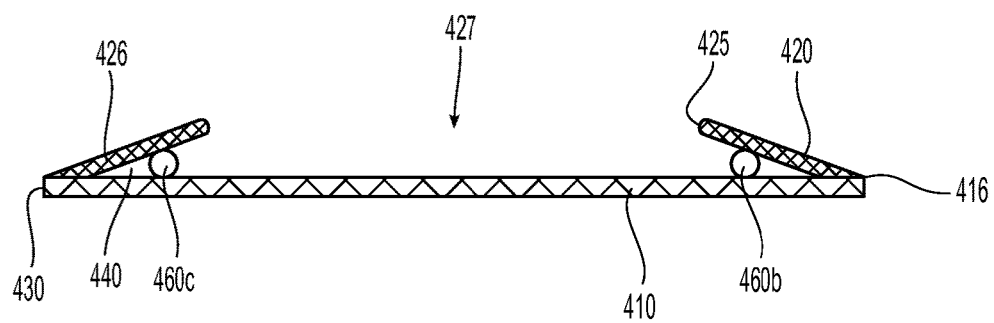
FIG. 4B is a side view of the embodiment depicted in FIG. 4A.

Turning now to FIGS. 4A-4B, a skirted hernia repair device 400 is shown which includes reinforcement members 460a-d that extend from inner peripheral edge 425 to outer peripheral edge 426 of skirt mesh layer 420. Similar to FIGS. 3A-3B, reinforcement members 460a-d can act as a guide for the fastening device (not shown). However, since reinforcement members 460a-d extend from inner peripheral edge 425 to outer peripheral edge 426, fastening device is more likely to enter the deepest portion of pocket 440.

In embodiments, as depicted in FIG. 4B, reinforcement member 460 may be positioned solely within pocket 440 and attach skirt mesh layer 420 to first mesh layer 410 without protruding from pocket 440. In embodiments, reinforcement member 460 may be an adhesive or sealant material which is placed within pocket 440 and allowed to cure, set or harden thereby attaching skirt mesh layer 420 to first mesh layer 410 without disrupting the topography of the outer surface of either layer. Skirt section may also be formed by heat or ultrasonic welding the skirt mesh layer 420 to the first mesh layer 410 at discrete locations.

Any biocompatible material may be used to form the skirted hernia repair devices described herein, including the first mesh layer, the skirt mesh layer and the reinforcement members. For example, the first mesh layer and the skirt mesh layer may be made from natural, synthetic, bioabsorbable and/or non-bioabsorbable materials. It should of course be understood that any combination of natural, synthetic, bioabsorbable and non-bioabsorbable materials may be used to form the first mesh layer and the skirt mesh layer described herein.

The term "bioabsorbable" as used herein is defined to include both biodegradable and bioresorbable materials. By bioabsorbable, it is meant that the materials decompose, or lose structural integrity under body conditions (e.g. enzymatic degradation or hydrolysis) or are broken down (physically or chemically) under physiologic conditions in the body such that the degradation products are excretable or absorbable by the body.

Representative natural bioabsorbable materials include: polysaccharides, such as alginate, dextran, chitin, hyaluronic acid, cellulose, collagen, gelatin, fucans, glycosaminoglycans, and chemical derivatives thereof (substitutions and/or additions of chemical groups, for example, alkyl, alkylene, hydroxylations, oxidations, and other modifications routinely made by those skilled in the art); and proteins, such as albumin, casein, zein, silk, and copolymers and blends thereof, alone or in combination with synthetic polymers.

Synthetically modified natural polymers include cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic bioabsorbable polymers include polyhydroxy acids prepared from lactone monomers, such as glycolide, lactide, caprolactone, ε-caprolactone, valerolactone, and δ-valerolactone, as well as pluronics, carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly (hydroxyvaleric acid); poly(lactide-co-(ε-caprolactone-)); poly(glycolide-co-(ε-caprolactone)); polycarbonates; poly (pseudo amino acids); poly(amino acids); poly(hydroxyalkanoate)s; polyalkylene oxalates; polyoxaesters; polyanhydrides; polyortho esters; and copolymers, block copolymers, homopolymers, blends, and combinations thereof. In certain embodiments, the first mesh layer and/or the skirt mesh layer may be formed using a combination of bioabsorbable and non-bioabsorbable polymers.

Some non-limiting examples of suitable non-bioabsorbable materials include polyolefins, such as polyethylene and polypropylene including atactic, isotactic, syndiotactic, and blends thereof polyethylene glycols; polyethylene oxides; ultra high molecular weight polyethylene; copolymers of polyethylene and polypropylene; polyisobutylene and ethylene-alpha olefin copolymers; fluorinated polyolefins, such as fluoroethylenes, including expanded polytetrafluoroethylene (ePTFE) and condensed polytetraflouroethylene c(PTFE), fluoropropylenes, fluoroPEGSs, and polytetrafluoroethylene; polyamides, such as nylon and polycaprolactam; polyamines; polyimines; polyesters, such as polyethylene terephthalate and polybutylene terephthalate; aliphatic polyesters; polyethers; polyether-esters, such as polybutester; polytetramethylene ether glycol; 1,4-butanediol; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvinylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as etheylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof.

The skirted hernia repair devices, including at least the first mesh layer and the skirt mesh layer, may be formed using any method within the purview of those skilled in the art. Some non-limiting examples include, weaving, knitting, braiding, crocheting, extruding, spraying, casting, molding, and combinations thereof. In some embodiments, the first mesh layer and the skirt mesh layer may be a two or three dimensional surgical mesh which is woven, knitted, braided, or crocheted from at least one first filament to form the layer. The at least one filament may be a monofilament or a multifilament.

In embodiments, the first mesh layer and the skirt mesh layer may be formed separately and combined along a seam using any suitable technique including weaving, knitting, braiding, crocheting, molding, suturing, welding, ultrasonics, gluing, and the like.

In embodiments, the first mesh layer and the skirt mesh layer may be initially formed as a single layer of mesh which is folded inwardly near the outer perimeter of the single layer of mesh to form the skirt mesh layer. The folded skirted mesh may be further processed to maintain the skirt mesh next to the first mesh layer in an overlapping position near the outer peripheral edge of each layer. Examples include thermosetting, ultrasonics, welding, pressing, knitting, braiding, weaving, crocheting and the like.

As depicted in the figures provided herein, the surface area of the first mesh layer is greater than the surface area of the skirt mesh layer. However, when the surface area of the first mesh layer is at least 1.5 times the surface area of the skirt mesh layer, the skirt mesh layer is more likely to be inverted during implantation and/or handling. In embodiments, the skirted hernia repair devices described herein include a first mesh layer having a surface area that is at least 1.5 times the surface area of the skirt mesh layer. In embodiments, the skirted hernia repair devices described herein include a first mesh layer having a surface area that is at least twice the surface area of the skirt mesh layer.

The reinforcement members described herein may be made from any biocompatible material, including the non-limiting exemplary list of natural, synthetic, bioabsorbable and/or non-bioabsorbable materials provided hereinabove. It should of course be understood that any combination of natural, synthetic, bioabsorbable and non-bioabsorbable materials may also be used to form the reinforcement members described herein.

The reinforcement members of the skirted hernia repair devices described herein may be formed using any method within the purview of those skilled in the art. Some non-limiting examples include, weaving, knitting, braiding, crocheting, extruding, spraying, dipping, casting, ultrasonics, welding, molding, and combinations thereof. In embodiments, the reinforcement members are filaments that fixedly attach the first mesh layer and the skirt mesh layer in the vicinity of the inner peripheral edge and/or the pocket. In embodiments, the reinforcement members are polymeric materials or tabs that fixedly attach the first mesh layer and the skirt mesh layer in the vicinity of the inner peripheral edge and/or the pocket. It is envisioned that a wide variety of other mechanical fasteners or fixtures may also be suitable for use as the reinforcement members. For example, in embodiments, the reinforcement members may be two part mechanical fasteners which are not fixedly attached, but rather can optionally be unattached when needed, such as the use of snaps, buttons, magnets and the like. In such embodiments, one part of the two part fastener may be positioned on the first mesh layer and the second part of the two-part fastener may be positioned on the skirt mesh layer.

Figure 5:
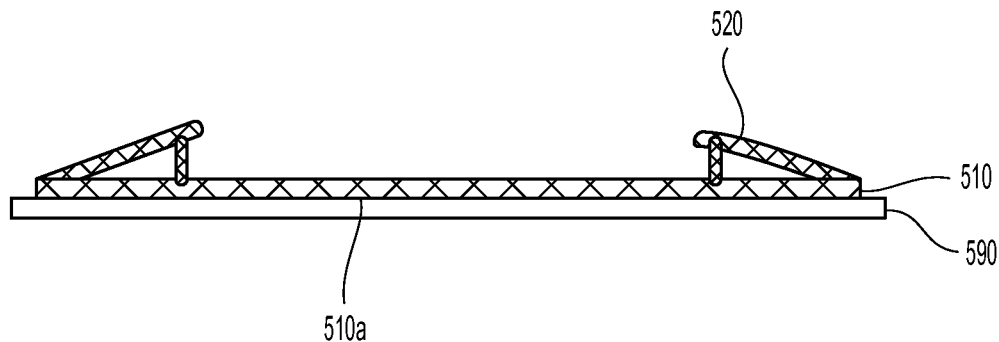
FIG. 5 is a side view of one embodiment of a skirted hernia repair device in accordance with the present disclosure.
Figure 6:
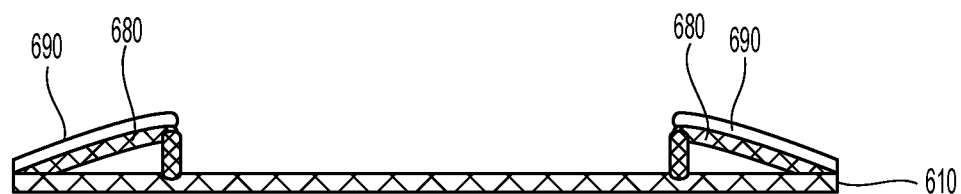
FIG. 6 is a side view of one embodiment of a skirted hernia repair device in accordance with the present disclosure; and, FIG. 7 is a side view of one embodiment of a skirted hernia repair device in accordance with the present disclosure.
Figure 7:
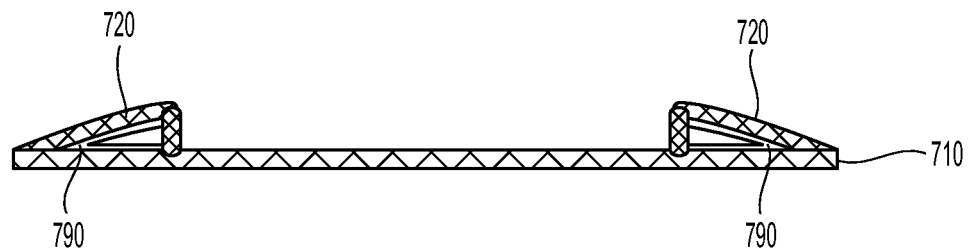

In embodiments, the skirted hernia repair device may include at least one additional layer. For example, in embodiments, the skirted hernia repair device may further include an adhesion barrier film which prevents the ingrowth of tissue between the barrier film and the layer(s) of mesh material. In embodiments, as illustrated in FIG. 5, an adhesion barrier film 590 may be positioned on the second side 510*a* of the first mesh layer 510, opposite the skirt mesh layer 520. In embodiments, as illustrated in FIG. 6, an adhesion barrier film 690 may be positioned on the outside of the skirt mesh layer 620, outside the skirted section 680. In still other embodiments, as illustrated in FIG. 7, an adhesion barrier film 790 may be positioned within the skirted section 780 between the first mesh layer 710 and the skirt mesh layer 720. Combinations of each of these embodiments are also envisioned.

Methods of using the skirted hernia repair devices are also described. In one embodiment, a method for repairing a tissue defect is described which includes: providing a skirted hernia repair device, positioning the skirted hernia repair device within a tissue defect such that a first mesh layer extends across the defect; and, securing the skirted hernia repair device to tissue. The skirted hernia repair device includes a first mesh layer, a skirt mesh layer, and at least one reinforcement member that connects the first mesh layer to the skirt mesh layer to prevent the skirt mesh layer from inverting. The first mesh layer includes a first side, a second side, and an outer peripheral edge. The skirt mesh layer is positioned on the first side of the first mesh layer; the skirt mesh layer includes an inner peripheral edge defining an opening. At least one reinforcement member that connects the first mesh layer to the skirt mesh layer to prevent the skirt mesh layer from inverting.

In another embodiment, a method for performing an intraperitoneal onlay procedure is described which includes: providing a skirted hernia repair device, positioning the skirted hernia repair device within a tissue defect such that a first mesh layer extends across the defect and optionally, an adhesion barrier positioned beneath the first mesh layer; and, securing the skirted hernia repair device to tissue. In embodiments, securing a skirt mesh layer of the skirted hernia repair device to the tissue. The skirted hernia repair device includes a first mesh layer, a skirt mesh layer, and at least one reinforcement member that connects the first mesh layer to the skirt mesh layer to prevent the skirt mesh layer from inverting. The skirted hernia repair device may optionally include an adhesion barrier. The first mesh layer includes a first side, a second side, and an outer peripheral edge. The skirt mesh layer is positioned on the first side of the first mesh layer; the skirt mesh layer includes an inner peripheral edge defining an opening. At least one reinforcement member that connects the first mesh layer to the skirt mesh layer to prevent the skirt mesh layer from inverting.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A skirted hernia repair device, comprising:
a first mesh layer having a first side, a second side, and an outer peripheral edge defining a center on the first side;
a skirt mesh layer positioned on the first side of the first mesh layer forming a pocket therebetween, the skirt mesh layer having an inner peripheral edge defining an opening; and,
at least one reinforcement member fixing the first mesh layer to the skirt mesh layer to prevent the skirt mesh layer from inverting, wherein each of the at least one reinforcement member is a polymeric tab extending from the skirt mesh layer inwardly towards the center first side of the first mesh layer over the inner peripheral edge and onto a portion of the first side of the first mesh layer inside the opening;
wherein the at least one reinforcement member comprises an edge configured to guide a fastening device into the pocket formed between the skirt mesh layer and the first mesh layer.

2. The skirted hernia repair device according to claim 1, wherein the edge at least one reinforcement member is a beveled edge.

3. The skirted hernia repair device according to claim 1, wherein the edge at least one reinforcement member is a rounded edge.

4. The skirted hernia repair device according to claim 1, wherein the at least one reinforcement member comprises a plurality of reinforcement members which are symmetrically positioned around the inner peripheral edge.

5. The skirted hernia repair device according to claim 1, wherein the at least one reinforcement member comprises a plurality of reinforcement members which are non-symmetrically spaced around the inner peripheral edge.

6. The skirted hernia repair device according to claim 1, wherein the at least one reinforcement member is positioned within the pocket of the device.

7. The skirted hernia repair device according to claim 1, wherein an outer peripheral edge of the skirt mesh layer is aligned with the outer peripheral edge of the first mesh layer.

8. The skirted hernia repair device according to claim 1, wherein an outer peripheral edge of the skirt mesh layer is not aligned with the outer peripheral edge of the first mesh layer.

9. The skirted hernia repair device according to claim 1, wherein the first mesh layer has a surface area that is at least 1.5 times larger than a surface area of the skirt mesh layer.

* * * * *